United States Patent [19]

Reif et al.

[11] Patent Number: 5,648,545
[45] Date of Patent: Jul. 15, 1997

[54] PREPARATION OF AMINES FROM NITRILES BY ALKYLATION WITH A NITROGEN COMPOUND IN THE PRESENCE OF A COPPER OXIDE/ZIRCONIUM OXIDE CATALYST

[75] Inventors: Wolfgang Reif, Frankenthal; Michael Hesse, Schifferstadt; Horst Zimmermann, Mannheim; Heinz Lingk, Bobenheim-Roxheim, all of Germany

[73] Assignee: BASF Aktiengesellschaft, Ludwigshafen, Germany

[21] Appl. No.: 494,955

[22] Filed: Jul. 5, 1995

[30] Foreign Application Priority Data

Jul. 4, 1994 [DE] Germany ............... 44 23 346.9

[51] Int. Cl.$^6$ ................................. C02C 209/48
[52] U.S. Cl. ........................... 564/470; 564/490
[58] Field of Search .................. 564/470, 490; 502/343, 345

[56] References Cited

U.S. PATENT DOCUMENTS

| | | | |
|---|---|---|---|
| 3,223,735 | 12/1965 | Scholz et al. | 260/583 |
| 3,260,752 | 7/1966 | Miller et al. | 260/583 |
| 3,398,196 | 8/1968 | Miller, Jr. et al. | 260/583 |
| 3,427,356 | 2/1969 | Baer et al. | 260/583 |
| 3,673,251 | 6/1972 | Frampton et al. | 260/563 D |
| 4,709,090 | 11/1987 | Nishibayashi et al. | 562/537 |
| 5,022,922 | 3/1991 | Irgang et al. | 106/287.11 |
| 5,075,506 | 12/1991 | Zimmerman | 564/490 |
| 5,166,433 | 11/1992 | Irgang et al. | 564/106 |
| 5,395,984 | 3/1995 | Yoneoka et al. | 568/811 |

FOREIGN PATENT DOCUMENTS

| | | |
|---|---|---|
| 382049 | 8/1990 | European Pat. Off. . |
| 484800 | 5/1992 | European Pat. Off. . |
| 4021230 | 1/1991 | Germany . |
| 5047991 | 3/1971 | Japan . |
| 5047910 | 8/1973 | Japan . |
| 2164034 | 3/1986 | United Kingdom . |

OTHER PUBLICATIONS

Archiv der Pharmacie vol. 271, pp. 439–445 (1933) (No translation).

*Primary Examiner*—Brian M. Burn
*Attorney, Agent, or Firm*—John H. Shurtleff

[57] ABSTRACT

Catalysts consisting of from 85 to 100 wt % of copper oxide and zirconium oxide and from 15 to 0 wt % of metal oxides of the subgroups Ib to VIIb and VIII of the Periodic Table and a process for the preparation of amines from nitriles and nitrogen compounds selected from the group comprising ammonia and primary and secondary amines, at temperatures of from 80° to 250° C. and pressures of from 1 to 400 bar using hydrogen in the presence of said catalysts.

10 Claims, No Drawings

PREPARATION OF AMINES FROM NITRILES BY ALKYLATION WITH A NITROGEN COMPOUND IN THE PRESENCE OF A COPPER OXIDE/ZIRCONIUM OXIDE CATALYST

The present invention relates to the use of catalysts consisting essentially of copper oxide and zirconium oxide, and optionally adding metal oxides of the subgroups Ib to VIIb and VIII of the Periodic Table, and to their use for the preparation of amines from nitriles and nitrogen compounds at elevated temperatures and pressures.

Archiv der Pharmazie 271 1933 439–445 reveals that in the reduction of nitriles the corresponding, secondary and tertiary amines are frequently formed in addition to primary amines. For the preparation of mixed secondary amines it is possible to add a primary or secondary amine during the hydrogenation of nitriles. However the reactions described were carried out using expensive palladium catalysts, and only poor space-time yields were achieved.

JP 50/47910 and JP 50/47911 reveal that secondary and tertiary ethylamine, respectively, can be prepared by the reaction of acetonitrile with ethylamine over Raney cobalt or Raney nickel. However, the discontinuous mode of operation described likewise makes only unsatisfactory space-time yields possible.

It was thus the object of the present invention to overcome the aforementioned drawbacks.

In accordance with the invention, we have found an improved process for the preparation of amines from nitriles and nitrogen compounds selected from the group comprising ammonia and primary and secondary amines, at temperatures of from 80° to 250° C. and pressures of from 1 to 400bar using hydrogen in the presence of catalysts consisting of from 85 to 100 wt % of the copper oxide and zirconium oxide components, optionally adding up to 15 wt % of at least one other metal oxide selected from the group consisting of the oxides of metals of subgroups Ib to VIIb and VIII of the Periodic Table.

The copper oxide/zirconium oxide catalysts of the invention consist of from 85 to 100 wt % of copper oxide and zirconium oxide and from 15 to 0 wt % of metal oxides of the subgroups Ib to VIIb and VIII of the Periodic Table, preferably from 90 to 100 wt % of copper oxide and zirconium oxide and from 10 to 0 wt % of metal oxides of the subgroups Ib to VIIb and VIII of the Periodic Table and more preferably from 95 to 100 wt % of copper oxide and zirconium oxide and from 5 to 0 wt % of metal oxides of the subgroups Ib to VIIb and VIII of the Periodic Table and especially from 98 to 100 wt % of copper oxide and zirconium oxide and from 2 to 0 wt % of metal oxides of the subgroups Ib to VIIb and VIII of the Periodic Table, and most especially from 99.5 to 100 wt % of copper oxide and zirconium oxide and from 0.5 to 0 wt % of metal oxides of the subgroups Ib to VIIb and VIII of the Periodic Table and their use for the preparation of amines from nitriles and nitrogen compounds selected from the group consisting of ammonia and primary and secondary amines, at temperatures of from 80° to 250° C. and pressures of from 1 to 400 bar.

The process of the invention can be carried out as follows:

The reaction is generally carried out without added solvents. During the reaction of starting compounds or products which are of high molecular weight, are highly viscous or are solid at room temperature it may be advantageous to make supplementary use of a solvent inert under the reaction conditions, such as tetrahydrofuran, dioxane, water or ethylene glycol dimethyl ether.

The reaction is usually carried out at temperatures ranging from 80° to 230° C., preferably from 90° to 170° C., and more preferably from 100° to 140° C. It is generally carried out under a pressure of from 1 to 400 bar. However, pressures of from 10 to 250 bar, particularly from 30 to 200 bar are preferably used.

The use of higher temperatures and a higher overall pressure is possible. The overall pressure in the reaction vessel, which is equal to the sum of the partial pressures of the aminating agents of the nitrile and the reaction products formed and any solvents used at the temperatures stated, is advantageously adjusted to the desired reaction pressure by forcing in hydrogen.

The hydrogen is passed to the reaction generally at a rate of from 5 to 400 L (STP) preferably at a rate of from 50 to 200 L (STP) per mole of nitrile component.

It may be advantageous in respect of the selectivity of the present process to mix the shaped catalyst elements in the reactor with inert packing elements so as to "dilute" them as it were. The proportion of said packing elements in such catalyst formulations can be from 20 to 80, preferably from 30 to 60, and more preferably from 40 to 50 percent by volume.

In practice the process is generally carried out as follows: the nitrile and the aminating agent are simultaneously fed to the catalyst, which is usually located in a preferably externally heated fixed bed reactor, at the desired temperature of reaction and the desired pressure. In this process the specific throughput is generally from 0.02 to 2, preferably from 0.05 to 1, and more preferably from 0.1 to 0.8 L of nitrile per liter of catalyst per hour.

The reactor can be operated in either the upward-flow mode or the downward-flow mode, ie the reactants can pass both upwardly and downwardly through the reactor. It is self-evident that the process can be carried out batchwise or continuously. In both cases the excess aminating agent can be circulated together with the hydrogen. If the conversion achieved by the reaction is not quantitative, the unconverted starting material can likewise be recycled to the reaction zone.

The aminating agent used in the hydrogenating amination of nitriles can be ammonia or preferably a primary or secondary, aliphatic or cycloaliphatic amine.

These aminating agents are preferably used for the preparation of non-symmetrically substituted di- or tri-alkylamines such as ethyldiisopropylamine and ethyldicyclohexylamine. For example, the following mono- and di-alkylamines are preferably used as aminating agents: methylamine, dimethylamine, ethylamine, diethylamine, propylamine, diisopropylamine, butylamine, pentylamine, hexylamine and cyclohexylamine.

The aminating agent can be used in a stoichiometric amount with respect to the nitrile group to be aminated. However, the process is preferably carried out using an excess of aminating agent, generally a more than 2fold molar excess per mole of nitrile group to be aminated. It is generally used in a 2 to 50fold molar excess, preferably a 5 to 25fold molar excess, and more preferably a 10 to 20fold molar excess per mole of nitrile groups to be converted. Higher excesses of primary or secondary amines are possible.

The excess aminating agent and the hydrogen can be removed from the effluent after this has advantageously been depressurized, and the aminated products obtained can be purified by distillation, liquid extraction, or crystallization.

The excess aminating agent and the hydrogen are advantageously recycled to the reaction zone. The same applies to any unconverted or incompletely converted nitrile component.

The catalysts of the invention are generally preferably used in the form of solid catalysts. By the term "solid catalyst" we mean a catalyst which, unlike a supported catalyst, consists of catalytically active material only. Solid catalysts can be used as follows: the catalytically active material, ground to a powder, is placed in the reaction vessel, or, the catalytically active material is milled, mixed with molding agent, molded, and tempered, to form shaped catalyst elements—for example balls, cylinders, rings, or spirals—which are then placed in the reactor.

Since the concentration data apply—unless otherwise stated—to the catalytically active material of the catalyst, the catalytically active material of the catalyst referred to below is defined as the sum of the materials of the catalytically active constituents in the catalyst calculated as oxide following its final heat treatment and prior to its reduction with hydrogen.

For the preparation of the solid catalysts various procedures are possible. For example, they can be obtained by forming a paste of pulverulent mixtures of the hydroxides, carbonates, oxides, and/or other salts of the components zirconium and copper and optionally of one or more metal oxides of the subgroups Ib to VIIb or VIII of the Periodic Table with water followed by extrusion and tempering of the material thus obtained.

However, precipitation methods are generally used for the preparation of the catalysts of the invention. Thus they can be obtained for example by concurrent precipitation of the aqueous salt solution containing elements by means of mineral bases in the presence of a slurry of a difficultly soluble, oxygen-containing zirconium compound followed by washing, drying and calcination of the precipitate obtained. Examples of difficultly soluble, oxygen-containing zirconium compounds are zirconium dioxide, zirconium oxide hydrate, and zirconium phosphates, borates and silicates. The slurries of the difficultly soluble zirconium compounds can be prepared by suspending fine-grained powders of these compounds in water with vigorous stirring. These slurries are advantageously obtained by precipitating the difficultly soluble zirconium compounds from aqueous zirconium salt solutions by means of mineral bases.

The catalysts of the invention are preferably prepared via concurrent precipitation (mixed precipitation) of all of its components. To this end, an aqueous salt solution containing the catalyst components is advantageously admixed, with heating and stirring, with an aqueous mineral base, in particular an alkali metal base—for example sodium carbonate, sodium hydroxide, potassium carbonate, or potassium hydroxide—until precipitation is complete. The nature of the salts used is not generally crucial. Since, when using this procedure, the water-solubility of the salts is the guiding factor, one criterion to be observed is sufficient water-solubility to allow for the preparation of these relatively highly concentrated salt solutions. It is to be regarded as self-evident that when selecting the salts of the individual components, naturally only those salts are chosen which have anions such as do not lead to false reactions, for example to undesirable precipitations or to the hindrance or prevention of precipitation due to complex formation.

Catalysts of the invention having particularly advantageous properties are obtainable by precipitating a portion of the zirconium component of the catalyst, advantageously from an aqueous zirconium salt solution separately in precipitating equipment by the addition of aqueous mineral bases. To the preferably freshly precipitated zirconium oxide hydrate thus obtained the remaining portion of the zirconium component of the catalyst can then be precipitated, together with the other catalytically active components, by mixed precipitation as described above.

In this process it is usually particularly advantageous to use a catalyst consisting of from 95 to 100 wt % of copper oxide and zirconium oxide and from 5 to 0wt % of metal oxides of the subgroups Ib to VIIb and VIII of the Periodic Table, preferably from 98 to 100 wt % of copper oxide and zirconium oxide and from 2 to 0 wt % of metal oxides of the subgroups Ib to VIIb and VIII of the Periodic Table, and more preferably from 99.5 to 100 wt % of copper oxide and zirconium oxide and from 0.5 to 0 wt% of metal oxides of the subgroups Ib to VIIb and VIII of the Periodic Table, and especially 100 wt % of copper oxide and zirconium oxide.

The internal ratio of copper oxide to zirconium oxide usually contains from 30 to 70 wt % of oxygen-containing copper compounds, preferably from 40 to 60 wt % of oxygen-containing copper compounds, more preferably from 45 to 55wt % of oxygen-containing copper compounds, and very preferably from 49 to 53 wt % of oxygen-containing copper compounds.

The precipitates obtained in these precipitation reactions are generally chemically uniform and consist inter alia of mixtures of the oxides, oxide hydrates, hydroxides, carbonates and insoluble and basic salts of the cited metals. Ageing of the precipitates may have a favorable effect on their filterability, ie, ageing achieved by leaving them to stand for a while after precipitation, optionally with heating or aeration.

The precipitates obtained in these precipitation reactions are processed in the usual manner to form the catalysts of the invention. After being washed, they are generally dried at from 80° to 200° C. and preferably from 100° to 150° C.

Following drying, the catalyst is advantageously conditioned, for example by milling it to a specific grain size, or by milling it and then mixing it with molding agents such as graphite or stearic acid followed by compression to shaped articles by means of a pelleting press, followed by tempering. The tempering temperatures used in this process are generally the same as those used during drying.

The catalysts prepared in this manner contain the catalytically active metals in the form of a mixture of their oxygen-containing compounds ie in particular in the form of oxides and mixed oxides.

The catalysts prepared in this manner are stored and, if desired, traded as such. Prior to their use as catalysts for the preparation of amines from nitriles they are usually subjected to preliminary reduction. However, they can be used without preliminary reduction if desired, in which case they are then reduced under the conditions of the hydrogenating amination by the hydrogen present in the reactor. To effect preliminary reduction the catalysts are generally first of all exposed to a nitrogen/hydrogen atmosphere at a temperature of from 150° to 200° C. over a period of from 12 to 20 h, and then treated in a hydrogen atmosphere at 200° C. for up to approximately 24 h. In this preliminary reduction process part of the oxygen-containing metal compounds present in the catalysts is reduced to form the corresponding metals, such that these, together with the various oxygen compounds, are present in the active form of the catalyst.

The substituents $R^1$, $R^2$, $R^3$, $R^4$, $R^5$ and the indices l, m, and n in the compounds I II and III independently have the following meanings:

$R^1$, $R^2$, $R^4$, $R^5$ hydrogen, $R^1$ preferably being hydrogen when $R^2$ is not hydrogen, $R^3$ $C_1$–$C_{200}$ alkyl preferably $C_1$–$C_8$ alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl, 2-ethylhexyl, n-decyl, 2-n-propyl-n-heptyl, n-tridecyl, 2-n-butyl-n-nonyl and 3-n-butyl-n-nonyl, more preferably isopropyl, 2-ethylhexyl, n-decyl, 2-n-propyl-n-heptyl, n-tridecyl, 2-n-butyl-n-nonyl and 3-n-butyl-n-nonyl and preferably $C_{40}$–$C_{200}$ alkyl such as polybutyl, polyisobutyl, polypropyl, polyisopropyl and polyethyl more preferably polybutyl and polyisobutyl, $R^1$, $R^2$, $R^3$ $C_3$–$C_{12}$ cycloalkyl preferably $C_3$–$C_8$ cycloalkyl such as cyclopropyl, cyclobutyl, cyclopentyl, cyclohexyl, cycloheptyl and cyclooctyl more preferably cyclopentyl, cyclohexyl and cyclooctyl, aryl, such as phenyl, 1-naphthyl, 2-naphthyl, 1-anthryl, 2-anthryl and 9-anthryl, preferably phenyl, 1-naphthyl and 2-naphthyl more preferably phenyl, $C_7$–$C_{20}$ oalkylaryl preferably $C_7$–$C_{12}$ alkylphenyl such as 2-methylphenyl, 3-methylphenyl, 4-methylphenyl, 2,4-dimethylphenyl, 2,5-dimethylphenyl, 2,6-dimethylphenyl, 3,4-dimethylphenyl, 3,5-dimethylphenyl, 2,3,4-trimethylphenyl, 2,3,5-trimethylphenyl, 2,3,6-trimethylphenyl, 2,4,6-trimethylphenyl, 2-ethylphenyl, 3-ethylphenyl, 4-ethylphenyl, 2-n-propylphenyl, 3-n-propylphenyl and 4-n-propylphenyl, $C_7$–$C_{20}$ aralkyl preferably $C_7$–$C_{12}$ phenylalkyl such as benzyl, 1-phenethyl, 2-phenethyl, 1-phenylpropyl, 2-phenylpropyl, 3-phenylpropyl, 1-phenylbutyl, 2-phenylbutyl, 3-phenylbutyl and 4-phenylbutyl more preferably benzyl, 1-phenethyl and 2-phenethyl, $R^3$ $C_1$–$C_{20}$ hydroxyalkyl preferably $C_1$–$C_8$ hydroxyalkyl and more preferably $C_1$–$C_4$ hydroxyalkyl such as hydroxymethyl, 1-hydroxyethyl, 2-hydroxyethyl, 1-hydroxy-n-propyl, 2-hydroxy-n-propyl, 3-hydroxy-n-propyl and 1-hydroxymethylethyl, $C_1$–$C_{20}$ alkyl substituted by amino and/or methylamino and/or dimethylamino and hydroxy, preferably $C_1$–$C_8$ alkyl substituted by amino and/or methylamino and/or dimethylamino and/or hydroxy, and more preferably $C_1$–$C_4$ alkyl substituted by amino and/or methylamino and/or dimethylamino and/or hydroxy such as N-(hydroxyethyl)aminoethyl and N-(aminoethyl)aminoethyl.

$C_2$–$C_{30}$ alkoxyalkyl preferably $C_2$–$C_{20}$ alkoxyalkyl and more preferably $C_2$–$C_8$ alkoxyalkyl such as methoxymethyl, ethoxymethyl, n-propoxymethyl, isopropoxymethyl, n-butoxymethyl, isobutoxymethyl, sec-butoxymethyl, tert-butoxymethyl, 1-methoxyethyl and 2-methoxyethyl more preferably $C_2$–$C_4$ alkoxyalkyl such as methoxymethyl, ethoxymethyl, n-propoxymethyl, isopropoxymethyl, n-butoxymethyl, isobutoxymethyl, sec-butoxymethyl, tert-butoxymethyl, 1-methoxyethyl and 2-methoxyethyl, $R^4$-(OCHR$^5$CH$_2$)$_n$, $R^1$ and $R^2$ $C_1$–$C_{20}$ alkyl preferably $C_1$–$C_8$ alkyl such as methyl, ethyl, n-propyl, isopropyt, n-butyl, isobutyl, sec-butyl, tert-butyl, n-pentyl, isopentyl, sec-pentyl, neopentyl, 1,2-dimethylpropyl, n-hexyl, isohexyl, sec-hexyl, n-heptyl, isoheptyl, n-octyl, isooctyl and more preferably $C_1$–$C_4$ alkyl such as methyl, ethyl, n-propyl, isopropyl, n-butyl, isobutyl, sec-butyl and tert-butyl, $R^4$ $C_1$–$C_{hd\,4}$ alkyl such as methyl, ethyl, n-propyl, isopropyl, n-butyl, isobutyl, sec-butyl and tert-butyl, preferably methyl and ethyl and more preferably methyl, $R^5$ methyl,

X oxygen,

N—$R^5$, l an integer from 2 to 4 such as 2, 3, and 4, preferably 2 and 3, more preferably 2, m an integer from 1 to 4 such as 1, 2, 3 and 4, preferably 2, 3 and 4, more preferably 2 and 3, n an integer from 2 to 10, preferably an integer from 2 to 8 such as 2, 3, 4, 5, 6, 7 or 8, more preferably an integer from 2 to 6 such as 2, 3, 4, 5 or 6.

The amines produced by the process of the invention are suitable inter alia as intermediates in the preparation of fuel additives (U.S. Pat. No. 3,275,554 DE-A 2,125,039 and DE-A 3,611,230), surfactants, medicines, plant protectants, and vulcanization promotors.

Examples

Catalyst preparation

Solution 1: zirconium acetate and copper nitrate are dissolved in distilled water, so that 27.4 liters of a solution are formed which contains 2.4 kg of zirconium (calculated as $ZrO_2$), and 5.251<g of copper (calculated as CuO). The pH of the solution is adjusted to ca 1 with $HNO_3$.

Solution 2: sodium carbonate is dissolved in distilled water such that a 20wt % solution containing soda is formed.

2.4 kg of zirconium dioxide are suspended in 60 liters of water, and the solution is heated to 80° C. The solutions 1 and 2 are concurrently fed to this well-stirred slurry, such that the pH in the precipitating vessel is kept at 5.5. On completion of the addition of the solution 1, the pH is raised to 7.5 by the addition of solution 2.

The mash of precipitated material thus obtained is washed and dehydrated in a filter press. The resulting powder is dried at 120° C. for 20 h, The powder thus obtained is mixed with 3 % of graphite, and compressed to pellets having a diameter of 5 min.

The resulting pellets have the following chemical composition: 52.6 wt % of CuO and 47.4 wt % of $ZrO_2$.

Example 1    Methylalkylation    of n-methylaminopropionitrile

A continuous high-pressure reactor was packed with 500 cm$^3$ of catalyst, and fed with 40 cm3/h of N-methylaminopropionitrile and 400 cm$^3$/h of liquid monomethylamine. The catalyst temperature was adjusted to 130° C. and the pressure in the reactor was adjusted to 200bar by simultaneously forcing in hydrogen. Excess monomethylamine was removed, by distillation, from the effluent following depressurization thereof. GC-analysis gave quantitative conversion and the following proportions of products present:

8,3 % of N-methylpropylenediamine
74,3 % N,N'-dimethylpropylenediamine
17,3 % other by-products Example 2

A continuous high-pressure reactor was packed with 500 cm³ of catalyst and fed with 100 cm³/h of N-methylaminopropionitrile and 400 cm³/h of liquid monomethylamine. The catalyst temperature was adjusted to 130° C. and the pressure in the reactor was adjusted to 200 bar by simultaneously forcing in hydrogen. Excess monomethylamine was removed, by distillation, from the effluent following depressurization thereof. GC-analysis gave >98wt % strength conversion and the following proportions of products present:

3.9 % of N-methylpropylenediamine
68.6 % N,N'-dimethylpropylenediamine
25.2 % other by-products

We claim:

1. In a catalytic amination process for the preparation of amines by reacting a nitrile with a nitrogen compound selected from the group consisting of ammonia, primary amines and secondary amines in the presence of hydrogen and at temperatures of from 80° to 250° C. and pressures of from 1 to 400 bar, the improvement which comprises:

carrying out the reaction in the presence of a catalyst consisting essentially of copper oxide and zirconium oxide as the catalytically active components in a ratio by weight of copper oxide (CuO) to zirconium oxide ($ZrO_2$) of from 30:70 to 70:30.

2. A process as claimed in claim 1 for the preparation of amines of the formula I

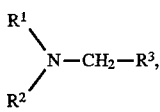    (I)

in which $R^1$ and $R^2$ denote hydrogen, $C_1$-$C_{20}$ alkyl, $C_3$-$C_{12}$ cycloalkyl, aryl, $C_7$-$C_{20}$ aralkyl and $C_7$-$C_{20}$ alkylaryl, $R^3$ denotes $C_1$-$C_{200}$ alkyl, $C_3$-$C_{12}$ cycloalkyl, $C_1$-$C_{20}$ hydroxyalkyl $C_1$-$C_{20}$ alkyl substituted by amino and/or methylamino and/or dimethylamino and/or hydroxy, $C_2$-$C_{30}$ alkoxyalkyl, $R^4$-$(XCHR^5CH_2)_n$-, aryl, $C_7$-$C_{20}$ aralkyl and $C_7$-$C_{20}$ alkylaryl, $R^4$ denotes hydrogen, $C_1$-$C_4$ alkyl, $R^5$ denotes hydrogen or methyl, x denotes oxygen or N—$R^5$, n is an integer from 2 to 30, l is an integer from 2 to 4, m is an integer from 1 to 4, from nitriles of the formula II

    (II), and nitrogen compounds of the general formula III

    (III)

in which $R^1$, $R^2$ and $R^3$ and $R^4$ have the aforementioned meanings.

3. A process as claimed in claim 1 wherein said weight ratio of CuO:$ZrO_2$ is from 40:60 to 60:40.

4. A process as claimed in claim 1 wherein said weight ratio of CuO:$ZrO_2$ is from 45:55 to 55:45.

5. A process as claimed in claim 1 wherein said weight ratio of CuO:$ZrO_2$ is from 49:51 to 53:47.

6. A process as claimed in claim 1 wherein the catalyst contains at least one additional metal oxide wherein the metal is an element selected from subgroups Ib to VIIb and subgroup VII of the Periodic Table in an amount of up to 15% by weight, based on the total weight of the catalyst.

7. A process as claimed in claim 6 wherein the additional metal is present in an amount of up to 10% by weight.

8. A process as claimed in claim 6 wherein the additional metal is present in an amount of up to 5% by weight.

9. A process as claimed in claim 6 wherein the additional metal is present in an amount of up to 2% by weight.

10. A process as claimed in claim 6 wherein the additional metal is present in an amount of up to 0.5% by weight.

* * * * *